US00PP22698P3

(12) United States Plant Patent
Davy

(10) Patent No.: US PP22,698 P3
(45) Date of Patent: May 1, 2012

(54) ***LAGERSTROEMIA (INDICA×FAURIEI)* PLANT NAMED 'JD900'**

(50) Latin Name: *Lagerstroemia (indica×fauriei)*
Varietal Denomination: JD900

(75) Inventor: John McNair Davy, Pace, FL (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 12/805,597

(22) Filed: Aug. 9, 2010

(65) Prior Publication Data

US 2012/0036604 P1 Feb. 9, 2012

(51) Int. Cl.
*A01H 5/00* (2006.01)

(52) U.S. Cl. ..... Plt./252

(58) Field of Classification Search ..... Plt./252
See application file for complete search history.

*Primary Examiner* — June Hwu

(74) *Attorney, Agent, or Firm* — Breiner & Breiner, LLC

(57) ABSTRACT

A new and distinct variety of *Lagerstroemia* (*indica×fauriei*) plant named 'JD900', characterized by its unique blooming time, dense, broad and spreading to weeping growth habit, fast growth rate and attractive light pink flowers which quickly change to white is disclosed.

1 Drawing Sheet

Genus species: *Lagerstroemia* (*indica×fauriei*).
Varietal denomination: 'JD900'.

FIELD OF INVENTION

The present invention relates to a new and distinct variety of Crapemyrtle of the genus *Lagerstroemia* and member of the Lythraceae family. This new Crapemyrtle variety, hereinafter referred to as 'JD900', was discovered by John McNair Davy in May, 1998 in Milton, Fla. 'JD900' is characterized by its unique blooming time, dense, broad and spreading to weeping growth habit, fast growth rate, and attractive light pink flowers which quickly change to white.

BACKGROUND OF THE INVENTION

'JD900' was found in a cultivated area as an openly pollinated seedling in a group of *Lagerstroemia* (*indica×fauriei*) 'Acoma' (unpatented) seedling plants being grown in a controlled environment in outside nursery in Milton, Fla. and was subsequently tested and evaluated primarily in Milton, Fla. and Loxley, Ala. The references in this application to these various evaluations will refer primarily to these two locations. The objective of the breeding program was to create new Crapemyrtle varieties which have unique blooming periods, bloom colors, and growth habits.

Asexual propagation of the new plant by cuttings has been under Mr. Davy's direction and control in Milton, Fla. and Loxley, Ala. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices.

1. Deciduous, multiple, or single stemmed shrub to small tree.

2. Dense, broad, spreading to weeping in nature.
3. Fast growth rate under normal fertilization and moisture conditions.
4. Unique blooming from early spring into fall.
5. Flower color is light pink as the buds open and quickly change to white.
6. Mature foliage changes to an attractive yellow color in the fall.
7. Attractive trunk structure when lower limbs are removed.
8. The grayish colored bark exfoliates to reveal a beige coloration.
9. Attractive trunk and stem structure during the winter.
10. Adaptable to a wide range of soil types from acidic to alkaline and sand to clay.
11. Heat and drought tolerant.
12. Easily propagated with softwood cuttings in the spring and summer.
13. Tolerates full sun.
14. Hardy to Zone 7.
15. Relatively pest resistant.
16. Good specimen plant.
17. Very desirable in planters
18. Requires little pruning but is tolerant if pruning is needed.

DESCRIPTION OF THE DRAWINGS

This new *Lagerstroemia* hybrid variety is illustrated by the accompanying photographic prints in which.

Figure 1:
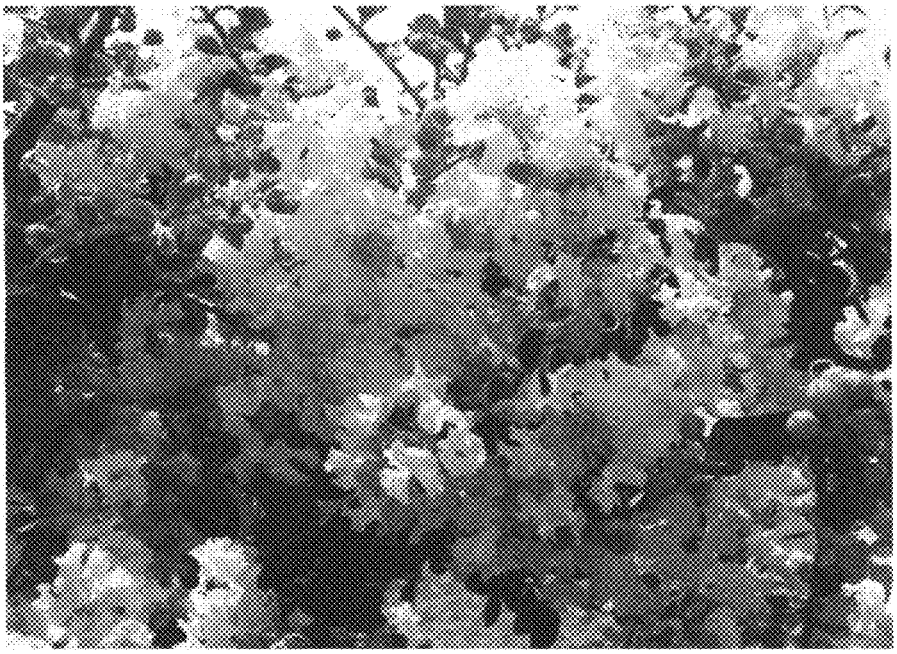
FIG. 1 is a photograph of a close-up of the flowers of the new *Lagerstroemia* hybrid cultivar of the present invention.
Figure 2:
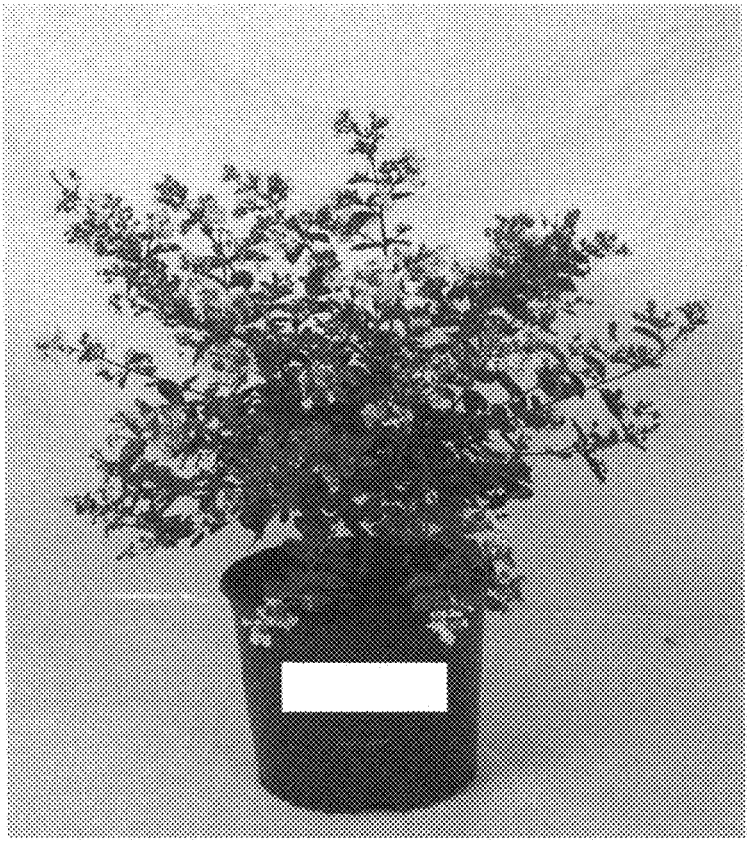
FIG. 2 is a photograph showing the dense, broad, spreading to weeping growth habit of a young three gallon (11.4 liter) plant of the new *Lagerstroemia* hybrid cultivar of the present invention.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart, 2001 edition. Description of colors in ordinary terms are presented where appropriate for clarity in meaning.

BOTANICAL DESCRIPTION OF THE PLANT

The following is a detailed description of the new variety of Crapemyrtle based on observations made of two year old plants grown in one to three gallon (3.8-11.4 Liter) containers in wholesale commercial production practices, in greenhouses, and in established landscape plantings.

DISTINCTIVE CHARASTERISTICS

TABLE 1

| Characteristic | *Lagerstroemia* x 'JD900' | *Lagerstroemia* x 'Acoma' | *Lagerstroemia* x 'Gamad V' U.S. Plant Pat. No. 17,411 |
|---|---|---|---|
| Height (Mature) | 6-10' (1.8-3 m) | 10-12' (3-3.6 m) | 3-4' (0.9-1.2 m) |
| Width (Mature) | 6-10' (1.8-3 m) | 10-12' (3-3.6 m) | 3-4' (0.9-1.2 m) |
| Leaf Length | 1-1 11/16" (2.5-4.3 cm) | 1½-2¾" (3.8-7 cm) | 1⅝" (4.2 cm) |
| Leaf Width | ⅝-1⅛" (1.6-2.8 cm) | ¾-1⅜" (1.9-3.5 cm) | 1 3/16" (2.1 cm) |
| Flower Color | Red-Purple G. 62D To White G. 155C | White G. 155C | Red-Purple G. 73B |
| Bloom Period | Mid May-September (Approx. 120 days) | Late June to September (Approx. 90 days) | Late June to September (Approx. 90 days) |
| Growth Habit | Dense, broad and spreading to weeping | Dense, broad and spreading to weeping | Compact, broad and rounded |
| Bark Color | Greyed Brown G. 199D | Greyed Brown G. 199C | Greyed-White G. 156A |

*Lagerstroemia* hybrid 'Acoma' (unpatented) and *Lagerstroemia* hybrid 'Gamad V' U.S. Plant Pat. No. 17,411 are well known in the industry and are comparable to 'JD900' in that all are deciduous and can be maintained as either a shrub or small tree. However, there are many differences. The growth habit of 'JD900' is dense, broad and spreading to weeping and 6-10' (1.8-3 m) tall compared to 'Acoma' which is a taller grower to 10-12' (3-3.6 m). 'Gamad V' has a mature height of 3-4' (0.9-1.2 m), a compact mounded growth habit and pink flowers.

CLASSIFICATION

Botanical: *Lagerstroemia* (*indica*×*fauriei*) 'JD900'.

Parentage: Openly pollinated seedling of *Lagerstroemia* (*indica*×*fauriei*) 'Acoma'.

Commercial: Deciduous tree or shrub.

Form: Dense, broad, spreading to weeping.

Height: 6'-10' (1.8-3 m).

Width: 6'-10' (1.8-3 m).

Growth rate: Fast under normal fertilization and moisture conditions. Softwood cuttings taken in the spring and summer produce cuttings in 1 to 2 months. Root development is vigorous and finely branched. These 6" (15 cm) tall cuttings planted in 3 gallon (11.4 liter) containers in the fall are 16" to 20" (41-51 cm) tall with profuse flowering the following year. The plant normally grows at the rate of about 10" to 14" (25-35 cm) per year and reaches a height of 6' to 10' (1.8-3 m) and a spread of 6' to 10' (1.8-3 m) at maturity while maintaining a dense habit due to the abundant branch development.

Foliage: Alternate to subopposite, simple, deciduous, elliptic and varying in size from 1" to 1 11/16" (2.5-4.3 cm) long and ⅝" to 1⅛" (1.6-2.8 cm) wide. The apex is acute and the base is cuneate. The margins are entire and the leaf venation is pinnate. The petioles are 1/16" to ⅛" (0.2-0.3 cm) long, 1/32" (0.08 cm) in diameter and puberulent. Midveins and laterals are puberulent and prominent on the upper surface and undersurface. Immature petioles, upper surface midveins and leaf margins are Greyed-Red Group 182B. The petioles mature to Green Group 137B and the margins mature to Yellow-Green Group 147A. Immature lateral veins are Yellow-Green Group 146D upper surface and undersurface and mature to Yellow-Green Group 146C upper surface and undersurface. Immature midveins are also Yellow-Green Group 146D undersurface. Mature midveins are Yellow-Green Group 146C upper surface and undersurface. These immature foliage colors last three to four weeks. The upper surface of the immature leaves is glossy, glabrous and is Green Group 137C and the underside is Yellow-Green Group 146D. This immature foliage matures to Green Group 137A upper surface and Green Group 146B undersurface in one to two weeks. Mature upper surface is glossy and glabrous and the undersurface is matte. Mature foliage color persists until the onset of cool weather in the fall. At this point the leaf color changes to Yellow Group 13B and persist until the leaves fall. Initial spring growth occurs in March. After the initial spring flush there is almost continuous growth until fall ending in about late October or early November. When grown in full sun, the internode length of this plant is ½" to ⅞" (1.3-2.2 cm). When grown in light shade the internode length is 1" to 1½" (2.6-3.8 cm). As would be expected, a plant grown in shade results in a taller, less dense plant with larger leaves.

Stems: The young shoots are slender, angled, glabrous and have a reddish pigmentation, Greyed-Red Group 182B when exposed to direct sunlight. Young shoots which are shaded from direct sunlight are Yellow-Green Group 144B. This new growth becomes Brown Group 200D and rounded in four to five weeks. After one or more years the stems become smooth, sinewy, Greyed-Brown Group 199B and eventually begin to exfoliate revealing the underlying color Greyed-Brown Group 199C. Branching habit is heavy. The pith is solid and uniform.

Flowers: Perfect, 1¼" to 1½" (3.1-3.8 cm) in diameter, ½" to ¾" (1.3-1.9 cm) in depth, non-fragrant, borne on dense, upright glabrous, 5" to 7" (12.7-17.8 cm) high, 4" to 5" (10.2-12.7 cm) wide terminal panicles, on current season's growth from mid-May through September. Flowers normally open from the base of the panicle progressing upward. Each panicle has from 8 to 12 racemes which have from 3 to 18 flowers each, resulting in 200 or more flowers per panicle. A mature plant can have hundreds of panicles. Flower buds are rotund, ¼" to ⅜" (0.6-0.9 cm) long, ¼"-⅜" (0.6-0.9 cm) wide and Greyed-Red Group 182B when exposed to direct sunlight. Young buds which are shaded from direct sunlight are Yellow-Green Group 144B. Flower color is light pink, Red-Purple Group 62D, as the buds open and quickly changes to white Group 155C front and back. The flowers are attached to pedicels which are ¼" to 7/16" (0.6-1.1 cm) in length, smooth, glabrous and Yellow-Green Group 144B. The peduncle of each raceme is from 1" to 4¼" (2.5-10.8 cm) long, tomentose and Yellow-Green Group 144B. Each flower has six petals that are ⅝" (1.6 cm) long, ½" (1.3 cm) wide; the blade is cordate-orbicular and crisped. The flower has 35 to 36 stamens in a cluster, 30 of which are shorter 5/16" (0.8 cm) long and located in the center. There are 5 to 6 longer 9/16" (1.4 cm) stamens which are located around the outside. The shorter stamens are Yellow-Orange Group 150D and the longer stamens are Yellow-Green Group 150C. The anthers are Yellow-Orange Group 20B. The pollen matures to Yellow Group 13B. The single pistil is ⅝" (1.6 cm) long and Yellow-Green Group 145B. The ovary is single, 1/16" (0.2 cm) in diameter, with no pubescence and Yellow-Green Group 150C. Each flower has six sepals that are 3/16" (0.5 cm) long by ⅛" (0.3 cm) wide, lanceolate and fused into a calyx. The calyx is ⅜" to ½" (0.9-1.3 cm) in diameter, ⅜" to 7/16" (0.9-1.1 cm) in depth, has entire margins and acuminate tips. The outer surface of the calyx is Greyed-Red Group 182B when exposed to direct sunlight and Yellow-Green Group 144B when shaded from direct sunlight. The inner surface is Yellow-Green Group 145C. Flowering period is from mid May through September. The self-cleaning blooms last eight to ten days on the plant in the garden.

Fruit: Broad-ellipsoidal six-valved dehiscent capsule, ⅜" to ½" (0.9-1.3 cm) in diameter. Summer fruit color Yellow-Green Group 143C ripens to Green Group 137A in the fall and persists as Green Group 137A through the winter. The mature capsule opens in the fall to release 12-16 glabrous winged seeds which are 3/16" to ¼" (0.5-0.6 cm) long and Brown Group 200D. Normal fruitset is heavy.

Culture: Grows well in a wide range of conditions. Tolerates full sun. Adaptable to a wide range of soil types from acidic to alkaline and sand to clay. Tolerates heat and drought when established. Reponds well to mulching and medium applications of fertilizer. Very little pruning is needed. Ideal for coastal regions and warmer parts of the Piedmont. Cold-hardiness and resistance to diseases and insects are comparable to the parent variety. Propagated with soft-wood cuttings in the spring and summer.

Disease and insect resistance: Resistance to diseases and insects common to *Lagerstroemia* has not been observed.

The exemplary embodiments herein disclosed are not intended to be exhaustive or to unnecessarily limit the scope of the invention. The exemplary embodiments were chosen and described in order to explain the present invention so that others skilled in the art may practice the invention.

It is claimed:

1. A new and distinct variety of *Lagerstroemia* plant named 'JD900' as illustrated and described herein.

* * * * *